United States Patent
Kasaoka

(10) Patent No.: US 10,898,155 B2
(45) Date of Patent: Jan. 26, 2021

(54) X-RAY DIAGNOSTIC APPARATUS

(71) Applicant: Toshiba Medical Systems Corporation, Otawara (JP)

(72) Inventor: Hayato Kasaoka, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 746 days.

(21) Appl. No.: 15/441,801

(22) Filed: Feb. 24, 2017

(65) Prior Publication Data

US 2017/0245826 A1 Aug. 31, 2017

(30) Foreign Application Priority Data

Feb. 29, 2016 (JP) .................................. 2016-038004

(51) Int. Cl.
*A61B 6/00* (2006.01)
*A61B 6/06* (2006.01)
*A61B 6/04* (2006.01)

(52) U.S. Cl.
CPC ............... *A61B 6/547* (2013.01); *A61B 6/06* (2013.01); *A61B 6/4441* (2013.01); *A61B 6/4452* (2013.01); *A61B 6/465* (2013.01); *A61B 6/0407* (2013.01)

(58) Field of Classification Search
CPC .............................. A61B 6/4441; A61B 6/4452
See application file for complete search history.

(56) References Cited

U.S. PATENT DOCUMENTS

| 5,014,292 | A | 5/1991 | Siczek et al. |
| 7,029,177 | B2 * | 4/2006 | Watanabe ............... A61B 6/06 378/197 |
| 8,831,173 | B2 | 9/2014 | Uehara et al. |

FOREIGN PATENT DOCUMENTS

| CN | 100405977 C | 7/2008 |
| CN | 104936527 A | 9/2015 |
| JP | H11-285492 A | 10/1999 |
| JP | 2004-105568 | 4/2004 |
| JP | 2006-271970 A | 10/2006 |
| JP | 2007-159987 | 6/2007 |

(Continued)

OTHER PUBLICATIONS

Combined Chinese Office Action and Search Report dated Feb. 22, 2019 in Patent Application No. 201710107972.4, 10 pages. (with English Translation of Category of cited Documents).

(Continued)

*Primary Examiner* — Dani Fox
(74) *Attorney, Agent, or Firm* — Oblon, McClelland, Maier & Neustadt, L.L.P.

(57) ABSTRACT

An X-ray diagnostic apparatus of an embodiment comprises a tabletop, an arm configured to support an X-ray tube and a detector such that the X-ray tube and the detector oppose to each other sandwiching a subject, a collimator configured to narrow an irradiation range of the X-ray, a detector moving equipment configured to cause the detector to make translational movement, and processing circuitry configured to control the collimator, and to accept information about an opening region of the collimator to acquire a movable range of the detector on a plane parallel to a detecting surface of the detector, and to cause, by the detector moving equipment, the detector to make translational movement relative to the X-ray tube within the acquired movable range.

15 Claims, 11 Drawing Sheets

(56) References Cited

FOREIGN PATENT DOCUMENTS

| JP | 2011-072582 A | 4/2011 |
| JP | 2013-240543 A | 12/2013 |
| JP | 5619535 | 11/2014 |
| JP | 2015-002938 A | 1/2015 |
| WO | WO 2014/148309 A1 | 9/2014 |

OTHER PUBLICATIONS

Japanese Office Action dated Oct. 29, 2019 in Japanese Patent Application No. 2016-038004, 3 pages.
Japanese Office Action dated Mar. 3, 2020, issued in Japanese Patent Application No. 2016-038004.
Chinese Office Action dated Jun. 3, 2020, issued in Chinese Patent Application No. 201710107972.4.
Japanese Office Action dated Jul. 7, 2020, issued in Japanese Patent Application No. 2016-038004.
Reconsideration Report by Examiner Before Appeal dated Nov. 5, 2020, issued in Japanese Patent Application No. 2016-038004.
Notice of Termination of Reconsideration by Examiner Before Appeal Proceedings dated Nov. 10, 2020, issued in Japanese Patent Application No. 2016-038004.

\* cited by examiner (1)

(2)

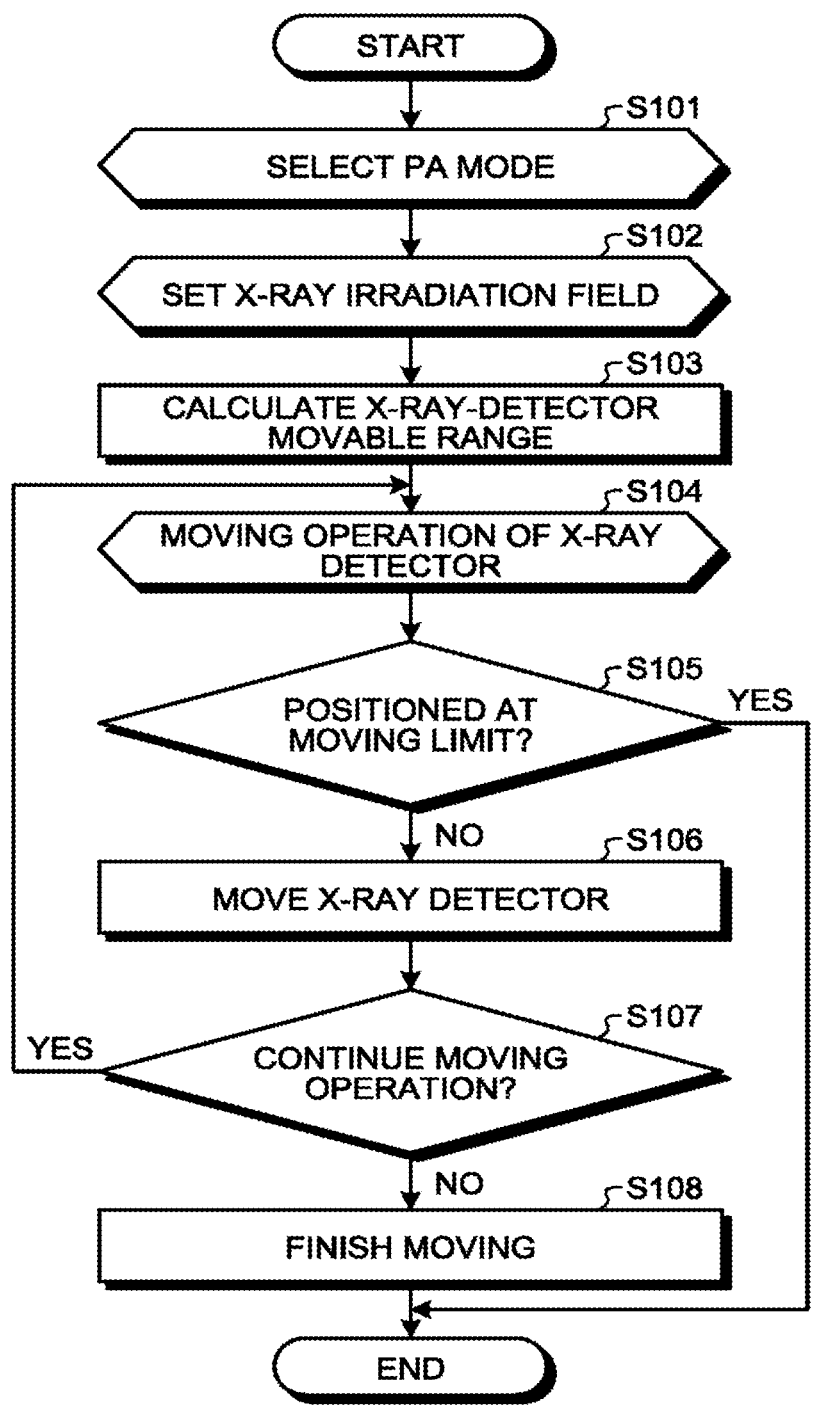

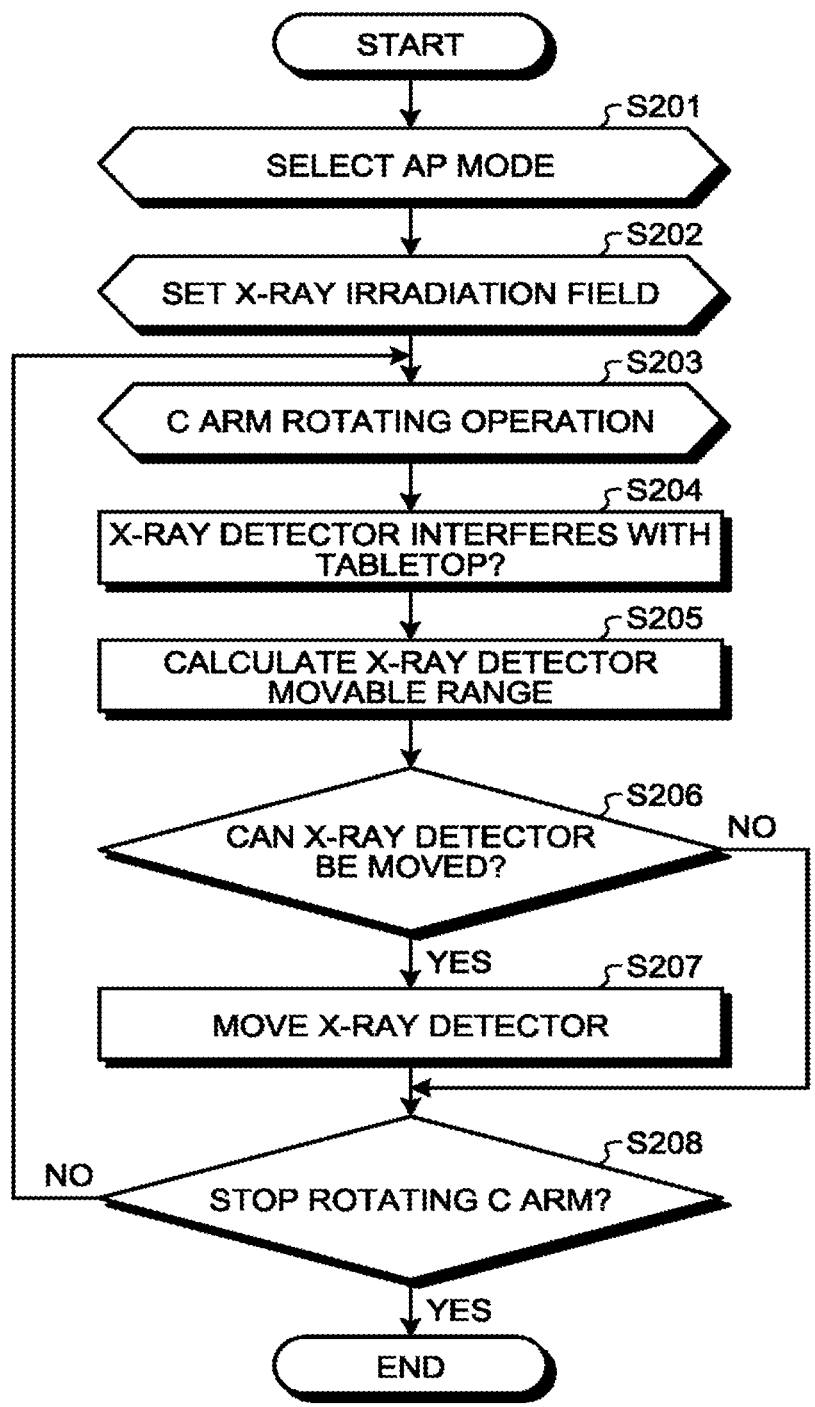

X-RAY DIAGNOSTIC APPARATUS

CROSS-REFERENCE TO RELATED APPLICATIONS

This application is based upon and claims the benefit of priority from Japanese Patent Application No. 2016-38004, filed on Feb. 29, 2016; the entire contents of which are incorporated herein by reference.

FIELD

Embodiments described herein relate generally to an X-ray diagnostic apparatus.

BACKGROUND

Conventionally, a procedure to insert a device such as a guide wire and a catheter (hereinafter, "device" collectively) into a blood vessel of a subject for the purpose of treating the blood vessel has been practiced. An X-ray diagnostic apparatus that acquires and displays contrast radiographs of a blood vessel to which a contrast agent has been injected to facilitate such a procedure has been known.

The operation to bring the device described above toward a subject portion is performed by an operator while referring to a monitor in a state in which a radioscopic image acquired by irradiating the subject with X-rays with an X-ray tube is displayed on the monitor.

In such a procedure using an X-ray diagnostic apparatus, it is necessary for an operator to proceed the procedure while watching a device insertion portion on a surface of a subject body at hand of an operator appropriately. However, an X-ray detector can interrupt the sight if it is positioned right above the subject body, when an operator sees the portion at hand.

Moreover, in a procedure in which the X-ray tube is arranged above a subject and the X-ray detector is arranged below the subject, there is a case in which a C arm that holds the X-ray tube and the X-ray detector opposing to each other is provided to perform the procedure. At this time, the X-ray detector and a tabletop can come into contact with each other.

BRIEF DESCRIPTION OF THE DRAWINGS

FIG. 7 is a flowchart showing one example of a flow of movement of the X-ray detector according to the first embodiment;

FIG. 12 is a flowchart showing one example of a flow of movement of the X-ray detector according to the second embodiment.

DETAILED DESCRIPTION

An X-ray diagnostic apparatus comprises a tabletop on which a subject is placed, an arm, a collimator, a detector moving equipment, and processing circuitry. The arm is configured to support an X-ray tube irradiating an X-ray and a detector that detects the X-ray such that the X-ray tube and the detector oppose to each other sandwiching the subject. The collimator is configured to narrow an irradiation range of the X-ray. The detector moving equipment is configured to cause the detector to make translational movement. The processing circuitry is configured to control the collimator. And the processing circuitry is configured to accept information about an opening region of the collimator, to acquire a movable range of the detector on a plane parallel to a detecting surface of the detector. And the processing circuitry is configured to cause, by the detector moving equipment, the detector to make translational movement relative to the X-ray tube within the acquired movable range.

Embodiments are explained below with reference to the drawings.

Figure 1:
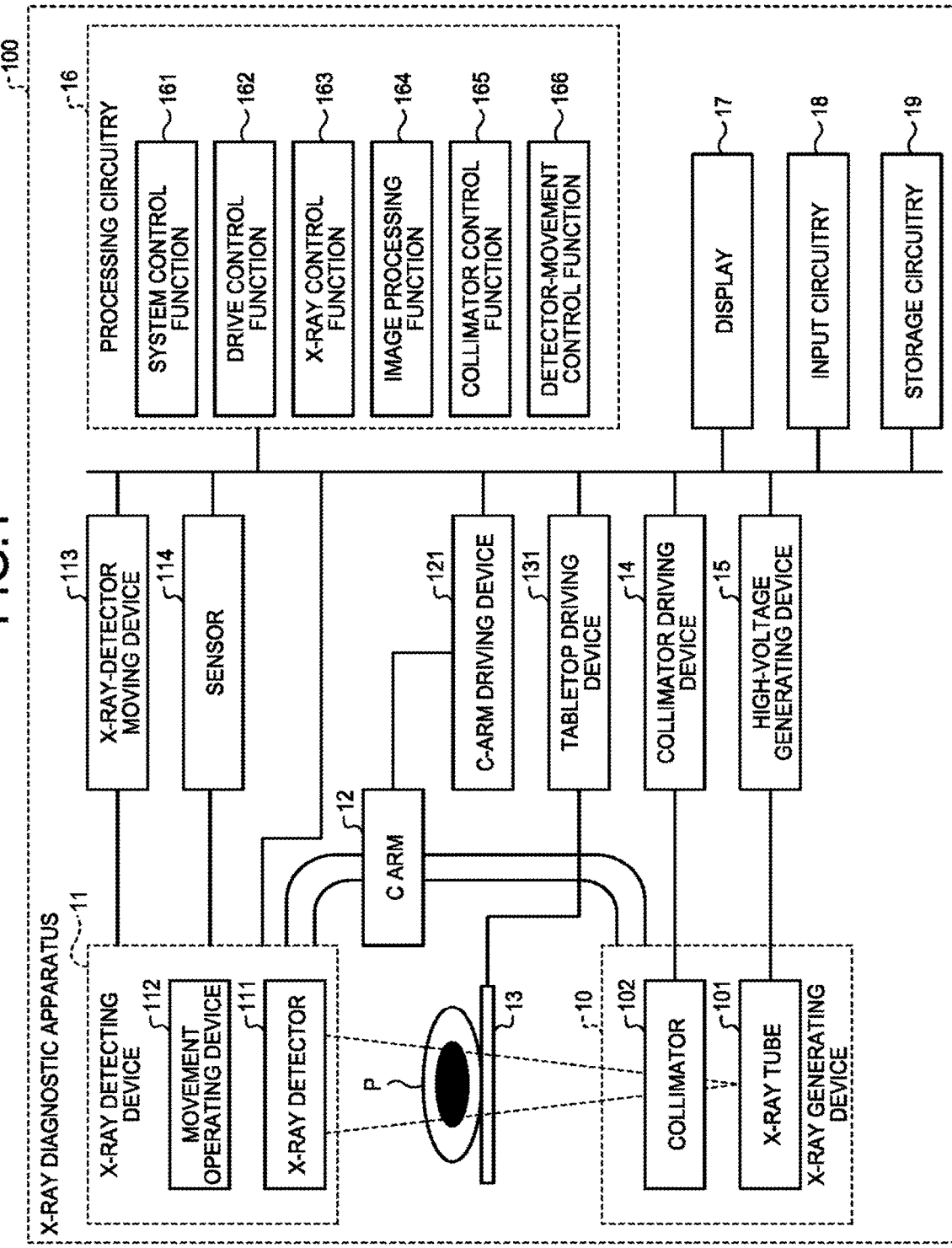
FIG. 1 is a block diagram showing a configuration of an X-ray diagnostic apparatus according to a first embodiment.

FIG. 1 is a block diagram showing a configuration of an X-ray diagnostic apparatus 100 according to a first embodiment. The X-ray diagnostic apparatus 100 in FIG. 1 includes a high-voltage generating device 15, an X-ray generating device 10 that irradiates a subject P with X-rays, and a collimator driving device 14 that performs driving control of a collimator 102.

The high-voltage generating device 15 is a power supply device that generates a high voltage to be applied between an anode and a cathode to outputs to an X-ray tube 101, to accelerate thermoelectrons that are generated from the cathode of the X-ray tube 101.

The X-ray generating device 10 includes the X-ray tube 101, and the collimator 102 that has a function of narrowing an irradiation range of an X-ray to irradiate only a region of interest.

The X-ray tube 101 is a vacuum tube that generates an X-ray by the high voltage generated by the high-voltage generating device 15, and accelerates a thermoelectron emitted from the cathode (filament) by the high voltage, and generates an X-ray by making this accelerated electron collide with a tungsten anode.

The collimator 102 is made of a material (for example, lead) that shields X-rays. The collimator 102 has a function of narrowing an X-ray irradiation range so as to irradiate only a region of interest of the subject P with an X-ray that is generated by the X-ray tube 101. For example, the collimator 102 has at least a pair of blades. As one example, the collimator 102 has four pieces of aperture blades, and narrows an X-ray irradiation range to an arbitrary size by sliding these aperture blades. That is, the collimator 102 narrows an irradiation range of an X-ray. Furthermore, a region that is formed by the aperture blades of the collimator 102, and through which an X-ray can pass is defined as an opening region by the collimator 102.

The collimator driving device 14 is a device that controls the opening region of the collimator 102 by driving the aperture blades of the collimator 102, and is configured with multiple motors and gears. Specifically, the collimator driving device 14 performs control of driving the aperture blades of the collimator 102 so that a region of interest on the subject P that is input by an operator through input circuitry 18 matches with an X-ray irradiation range. The region of interest on the subject P is a region that includes a lesion or a portion to be treated of the subject P, and is specified, for example, by an operator on an X-ray image. Moreover, the collimator driving device 14 also has a function of detecting the size of the opening region by the collimator 102, The method of detecting the opening region by the collimator 102 can be based on detection of an area of the opening region, or based on detection of an amount of movement of the aperture blades.

Figure 2:
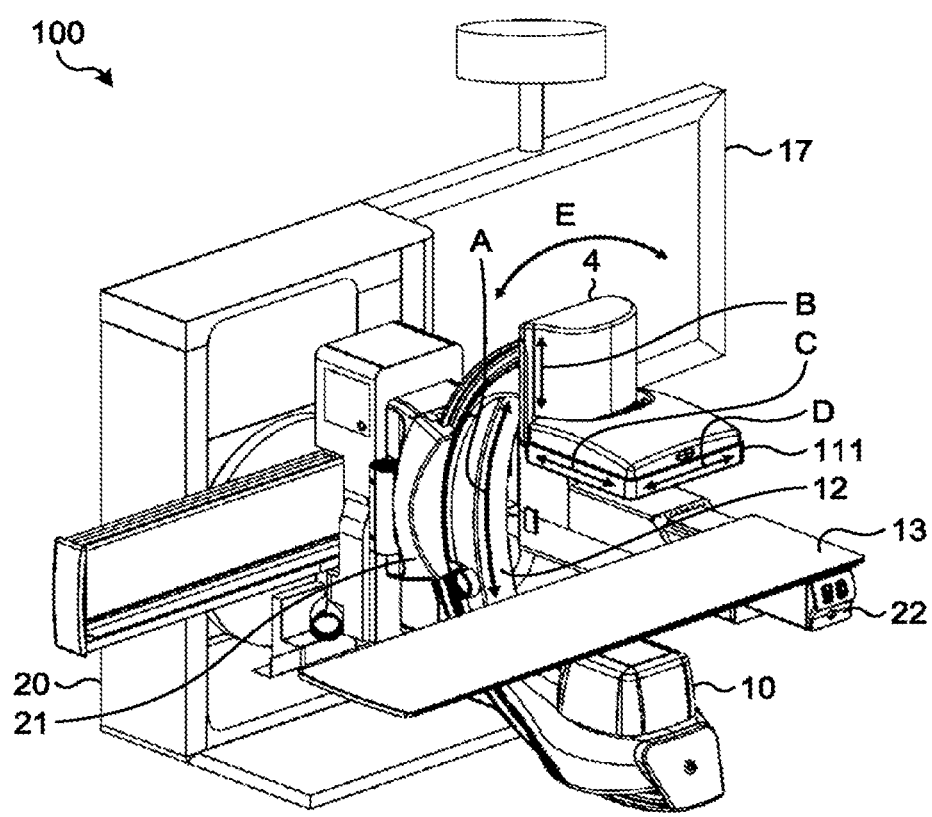
FIG. 2 is an external view of the X-ray diagnostic apparatus according to the first embodiment.

The X-ray diagnostic apparatus 100 includes a C arm 12, a C-arm driving device 121, a tabletop 13, and a tabletop driving device 131. FIG. 2 is referred to explain the C arm 12 and the tabletop 13.

FIG. 2 is an external view of the X-ray diagnostic apparatus 100 according to the present embodiment. A frame 20, the C arm 12, and the tabletop 13 are explained by using FIG. 2.

The frame 20 supports the C arm 12 through a C-arm connecting device 21, and is a casing to hold the tabletop 13 through a tabletop holding device 22.

The C arm 12 is connected to the frame 20 through the C-arm connecting device 21. The C arm 12 is a C arm that supports the X-ray tube 101 irradiating X-rays and an X-ray detector 111 (detector) that detects the X-rays such that the X-ray tube 101 and the X-ray detector 111 oppose to each other sandwiching the subject P. Specifically, the C arm 12 supports them so that an X-ray irradiation direction of the X-ray tube 101 that irradiates X-rays and the X-ray detector 111 that detects the X-rays oppose to each other sandwiching the subject P therewith. The C-arm connecting device 21 is a casing that holds the C arm 12 so as to be able to slide along the shape of the C arm 12 (arrow A). The C arm 12 can rotate in such a direction that the C arm 12 can be turned upside down by 180 degrees about the C-arm connecting device 21 as the center (arrow E). The C arm 12 has a structure that enables to X-ray radiograph the subject P that is laid on the tabletop 13 by supporting the components such that the X-ray irradiation direction of the X-ray generating device 10 and an X-ray detecting device 11 are opposed to each other, sandwiching the subject P and the tabletop 13.

The X-ray detector 111 that is attached to the C arm has a structure that enable to move in a vertical direction (arrow B) and a horizontal direction (arrows C and D) relative to a floor.

On the tabletop 13, the subject P is placed. For example, the tabletop 13 is a plate-shaped structure on which the subject P is lied at the time of X-ray imaging, and is connected to the frame 20 through the tabletop holding device 22. The tabletop holding device 22 is a casing that holds the tabletop 13. The C arm 12 is a C arm that is arranged so as to sandwich the tabletop 13 along a short side direction of the tabletop 13 as shown in FIG. 2.

Explanation returns to the block diagram in FIG. 1.

The C-arm driving device 121 reads a driving signal from a drive control function 162 of processing circuitry 16 and causes the C arm 12 to make a sliding movement, a rotating movement, and rectilinear movement. The C-arm driving device 121 is configured with a power source such as multiple motors. Moreover, a C-arm state detector not shown to detect an angle, posture, or positional information of the C arm is provided in the C-arm driving device 121. The C-arm state detector is for example, configured with a potentiometer that detects a rotation angle and an amount of movement, an encoder, which is a position detection sensor, and the like. As the C arm 12 or the tabletop 13 moves, a positional relationship between the X-ray generating device 10 and the X-ray detecting device 11 with respect to the subject P changes. More specifically, as for the encoder, for example, a so-called absolute encoder of a magnetic type, a brush type, a photoelectric type, or the like can be used. Moreover, the C-arm state detector can be configured with various kinds of position detecting mechanisms, such as a rotary encoder that outputs a rotational displacement as a digital signal and a linear encoder that outputs a linear displacement as a digital signal. Furthermore, the mechanism that enables movement of the C arm 12 explained above is just one example, and the present embodiment is not limited thereto.

The tabletop driving device 131 reads a driving signal from the drive control function 162 of the processing circuitry 16, and moves the tabletop 13 in a horizontal and a vertical direction with respect to a floor. Moreover, the tabletop driving device 131 is configured with a power source such as multiple motors. As the C arm 12 or the tabletop 13 moves, a positional relationship between the X-ray generating device 10 and the X-ray detecting device 11 with respect to the subject P changes.

The X-ray diagnostic apparatus 100 includes the X-ray detecting device 11 that detects an X-ray that has passed through the subject P, and that generates X-ray projection data reflecting an amount of detected X-ray.

The X-ray detecting device 11 is constituted of the flat-shaped X-ray detector 111 that converts an X-ray passed through the subject P into an electric charge and accumulates it, a movement operating device 112 that accepts an input operation from an operator, and determines a moving direction of the X-ray detector 111, an X-ray-detector moving device 113 that moves the X-ray detector 111 in a parallel direction to a detector surface, and a sensor that detects positional information on a plane parallel to the detector surface of the X-ray detector 111.

The X-ray detector 111 is configured, for example, with a flat panel detector (FPD). The FPD is constituted of minute detecting devices that are aligned two-dimensionally in a column direction and a line direction. Each detecting device detects an X-ray, and is constituted of a photoelectric film that generates an electric charge according to an amount of incident X-ray, a charge accumulation capacitor that accumulates the electric charge generated by this photoelectric film, and a thin film transistor (TFT) that outputs the electric charge accumulated in the charge accumulation capacitor at predetermined timing. The X-ray detector 111 includes projection-data generating circuitry that outputs the electric charge accumulated in the TFT, and that generates projection data from the output electric charge. The projection data is output to storage circuitry 19 once.

The movement operating device 112 is constituted of, for example, various kinds of switches, a touch panel, a sensor (contact sensor, acceleration sensor, optical sensor), and the like arranged on a side surface of the X-ray detector 111. The movement operating device 112 accepts an input operation from an operator, and transmits a command to move the X-ray detecting device 11 to the X-ray-detector moving device 113. Moreover, the movement operating device 112 is not limited to the structure that is arranged on a sides surface of the X-ray detector 111, and can be arranged, for example, on the tabletop 13 on which the subject P is placed. By arranging the movement operating device 112 on the tabletop 13, the position of the movement operating device 112 does not change even if the X-ray detector 111 is moved by operating the movement operating device 112, and therefore, it becomes easier for an operator to operate the movement operating device 112.

Figure 3:
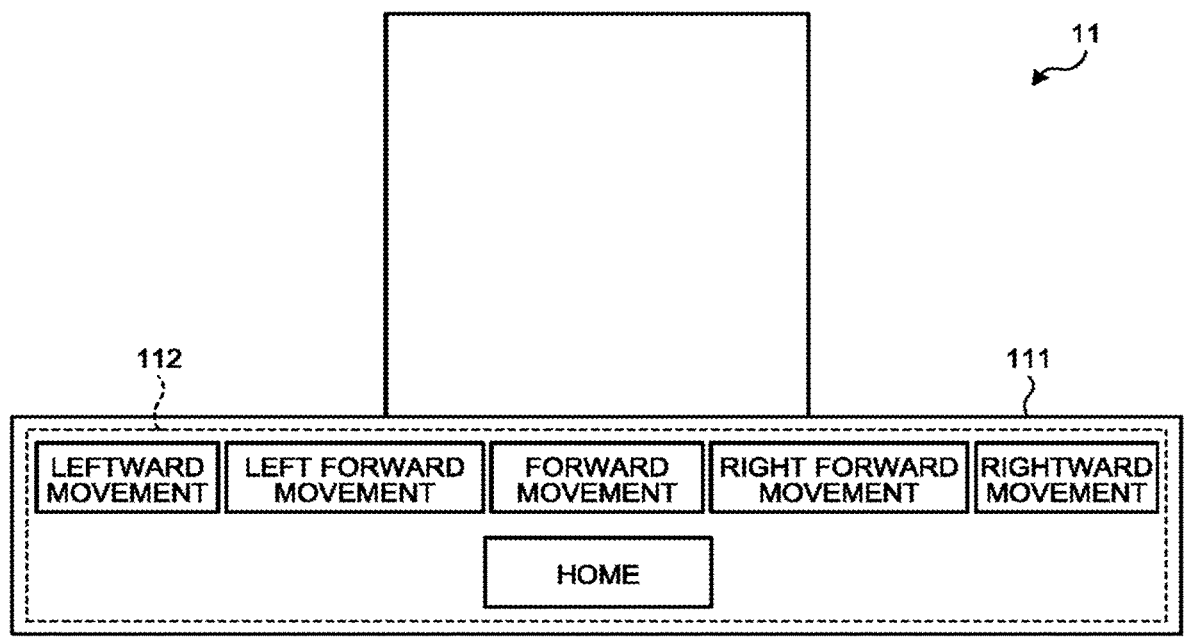
FIG. 3 shows an arrangement example of a switch to specify a moving direction of an X-ray detector according to the first embodiment.

FIG. 3 is a diagram for explaining one example of a configuration of the movement operating device 112. For example, the movement operating device 112 is arranged on a side surface of the X-ray detector 111 on an opposite side to the frame 23. For example, the movement operating device 112 has plural switches arranged thereon to accept a desired moving direction from an operator, and has such a configuration that an operator can select a desired switch according to a desired moving direction. That is, the movement operating device 112 in FIG. 3 is provided in the X-ray detector 111 as the input circuitry 18, and is constituted of switches to accept a moving direction of the X-ray detector 111 from an operator. As one example of the switches arranged a the movement operating device 112, those of "leftward movement", "left forward movement", "forward movement", "right forward movement", "rightward movement", "home", and the like from a front direction of the surface on which the movement operating device 112 is arranged can be prepared. The respective moving directions are explained in detail in explanation about a detector-movement control function 166 of the processing circuitry 16 described later.

The X-ray-detector moving device 113 (detector moving equipment) causes the X-ray detector 111 to make translational movement. For example, the X-ray-detector moving device 113 accepts information about a moving direction of the X-ray detector 111 from the movement operating device 112, and drives the X-ray detector 111 to move it. The X-ray-detector moving device 113 is configured with multiple motors and gears. Furthermore, the X-ray-detector moving device 113 reads an X-ray irradiation rang that is determined by the size of an opening region by the collimator from a collimator control function 165 of the processing circuitry 16 described later, and moves the X-ray detector 111 within the X-ray irradiation range. The X-ray irradiation range indicates a range in which an X-ray is irradiated on the X-ray detector 111. Details of the X-ray-detector moving device 113 are explained using FIG. 4, FIG. 5A, and FIG. 5B.

Figure 4:
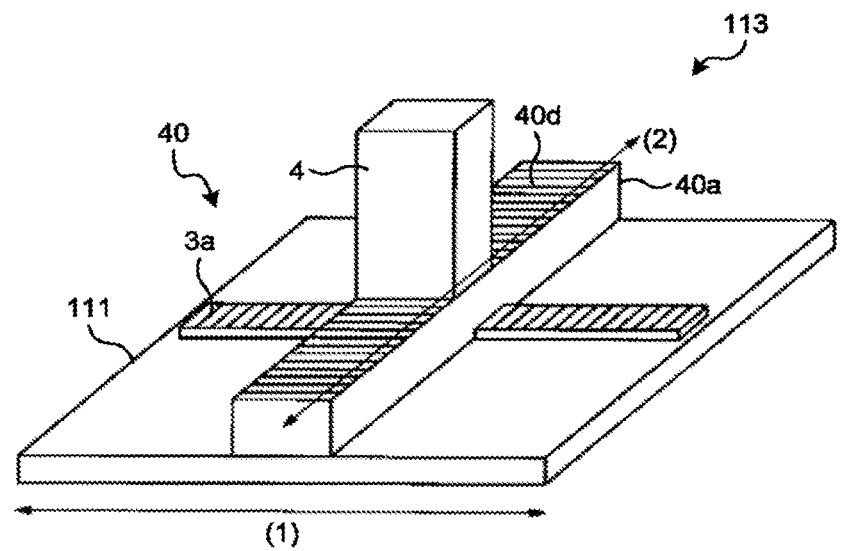
FIG. 4 is a diagram for explaining parallel movement mechanism of the X-ray detector according to the first embodiment.

FIG. 4 shows a configuration example of the X-ray-detector moving device 113. As shown in FIG. 4, the X-ray-detector moving device 113 has a structure that two axes perpendicular to each other (directions of (1) and (2) shown in the drawing) move independently. For the movement of the respective axes, an amount of movement is calculated within a range not exceeding a movable range of the X-ray detector 111 calculated by the detector-movement control function 166 of the processing circuitry 16 relative to the moving direction input from the movement operating device 112. For example, the X-ray detector 111 is configured to move when an operator operates the movement operating device 112 by pressing it or the like, and to stop when an operator releases the movement operating device 112. Moreover, it can be configured such that the X-ray detector 111 automatically moves until the X-ray detector 111 reaches a moving limit of the X-ray detector 111 calculated by the detector-movement control function 166 of the processing circuitry 16 when the movement operating device 112 accepts an input operation by an operator.

Figure 5A:
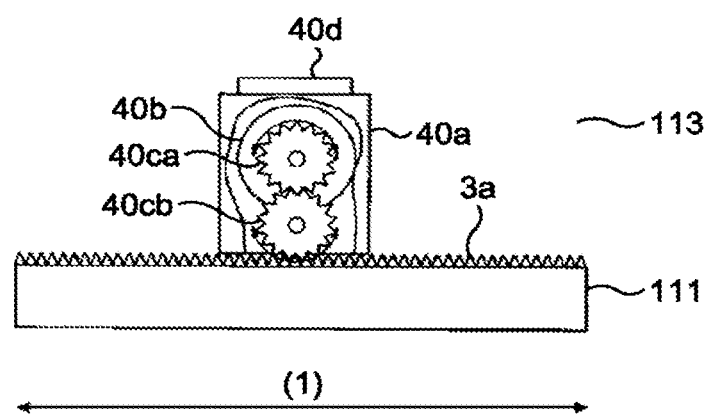
FIG. 5A is a diagram for explaining details of the parallel moving mechanism of the X-ray detector according to the first embodiment.

More specifically, as for the parallel movement in the direction (1) in FIG. 4, as shown in FIG. 5A, with a structure in which a detector back gear 3a formed on a rear surface of the X-ray detector 111 and a gear 40cb that is connected to a motor 40b through a gear 40ca engage each other, and with forward and reverse rotation of the motor 40b, the parallel movement in the direction (1) is enabled. A power supply line to drive the motor 40b is wired from the processing circuitry 16 described later and the like to the motor 40b of a moving unit 40a through the C arm 12. Furthermore, a control-signal transmission line of the motor 40b is also wired through the same path.

Figure 5B:
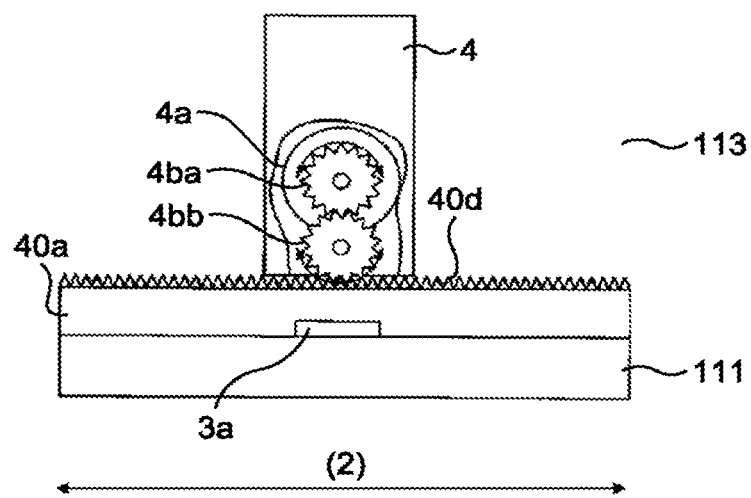
FIG. 5B is a diagram for explaining details of the parallel moving mechanism of the X-ray detector according to the first embodiment.

Moreover, as for the parallel movement in the direction (2) in FIG. 4, as shown in FIG. 5B, with a structure in which a moving-unit back gear 40d and a gear 4bb that is connected to a motor 4a that is mounted near a central portion of a detector supporting device 4 through a gear 40ba engage each other, and with forward and reverse rotation of the motor 4a, the parallel movement in the direction (2) is enabled. A power supply line to drive the motor 4a is wired from the processing circuitry 16 described later and the like to the motor 4a through the C arm 12. Furthermore, a control-signal transmission line of the motor 4a is also wired through the same path. The detector supporting device 4 is a casing that connects the C arm 12 and the X-ray detecting device 11.

As described above, by operating the two axes shown in FIG. 5A and FIG. 5B independently, the parallel movement including an inclined direction of the X-ray detector 111 is enabled.

Furthermore, the X-ray-detector moving device 113 in the first embodiment can be configured to reduce the moving speed of the X-ray detector 111, for example, when the moving limit of the X-ray detector 111 is close. The moving limit herein is a range that the X-ray detector 111 exceeds the X-ray irradiation range if the X-ray detector 111 moves toward a direction specified by an operator. As a method of reducing the moving speed of the X-ray detector 111, for example, the moving speed can be reduced in stages as it approaches the moving limit, or can be reduced linearly in proportion to a distance to the moving limit. By this way, an operator can be notified that the X-ray detector 111 cannot be moved toward a direction specified by an operator. Moreover, the method of informing the limit of the movable range of the X-ray detector 111 to an operator is not limited to one by the moving speed of the X-ray detector 111. For example, it can be informed to an operator by sounds, or can be informed on a display 17. Furthermore, the limit of the movable range of the X-ray detector 111 can be informed by emitting light from the switches constituting the movement operating device 112 or the like, or can be informed by emitting light from a lamp that is additionally arranged on the side surface of the X-ray detector 111, or the like.

Figure 6A:
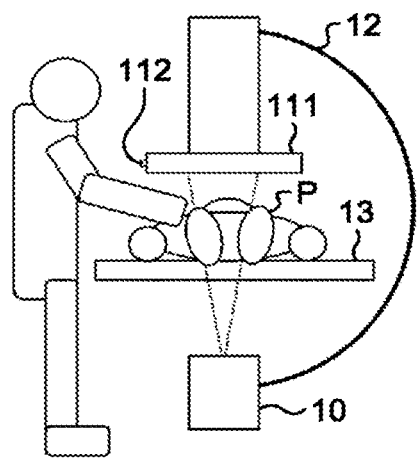
FIG. 6A is a schematic diagram showing one example of a moving method of the X-ray detector according to the first embodiment.
Figure 6B:
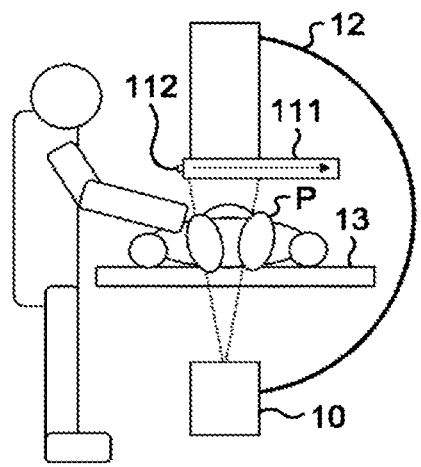
FIG. 6B is a schematic diagram showing one example of a moving method of the X-ray detector according to the first embodiment.

FIG. 6A and FIG. 6B show one example of movement of the X-ray detector 111 in the first embodiment. For example, in a state shown in FIG. 6A, the X-ray detector 111 interrupts the sight of an operator, and an operator cannot be aware of a state at hand when an operator performs treatment on the subject P. Therefore, an operator selects a moving direction of the X-ray detector 111 by operating the movement operating device 112 arranged on the side surface of the X-ray detector 111, and the X-ray detector 111 moves in a direction selected by an operator as shown in FIG. 6B. Thus, an operator can be aware of the state at hand during the treatment without the sight being interrupted by the X-ray detector 111.

Explanation returns to the block diagram in FIG. 1. The X-ray diagnostic apparatus 100 includes the display 17, the input circuitry 18, and the storage circuitry 19.

The display 17 (display) includes a radioscopic monitor to display various kinds of X-ray image data generated by an image processing function 164 of the processing circuitry 16 described later, a reference monitor that performs image display of other modality and the like, and a system monitor that displays various kinds of input/setting screens to control inputs of imaging conditions and the like and the system. These monitors can be configured separately, or can be implemented by dividing a display region of a large monitor. For example, the display 17 displays an X-ray image that is generated based on an X-ray detected by the X-ray detector 111.

The input circuitry 18 includes an input device, such as a trackball, a joy stick, a main console having various kinds of buttons, a keyboard, and a mouse, and a footswitch, and the like. With such an input interface, input of subject information, setting of an X-ray irradiation condition (an source image distance (SID) value, a tube voltage, a tube current, and the like) and an image scaling factor, selection of an image sequence such as rotation imaging, setting of an imaging position and direction of a subject, input of various commands such as an imaging start command. That is, the input circuitry 18 accepts input information from an operator.

The storage circuitry 19 stores projection data that is generated from X-ray detection data detected by the X-ray detector 111, X-ray image data that is generated from the projection data, and various functions performed by the processing circuitry 16 in a form of program. The storage circuitry 19 is configured with, for example, a semiconductor memory device such as a random-access memory (RAM) and a flash memory, a hard disk, an optical disk, or the like.

The processing circuitry 16 is constituted of a system control function 161, the drive control function 162, an X-ray control function 163, the image processing function 164, the collimator control function 165, and the detector-movement control function 166.

The system control function 161 overall controls the drive control function 162, the X-ray control function 163, the image processing function 164, the collimator control function 165, and the detector-movement control function 166.

The drive control function 162 accepts information relating to the drive of the C arm 12 and the tabletop 13 input from the input circuitry 18, and controls the C-arm driving device 121 and the tabletop driving device 131.

The X-ray control function 163 reads information from the system control function 161, and controls the X-ray irradiation condition, such as a tube current, a tube voltage, and an irradiation duration, in the high-voltage generating device 15.

The image processing function 164 acquires projection data from the storage circuitry 19 to generate an X-ray image.

The collimator control function 165 controls the collimator 102. For example, the collimator control function 165 controls opening and closing of the blades in the collimator 102, to control the collimator 102. As one example, the collimator control function 165 accepts an input signal input by an operator through the input circuitry 18, and drives the collimator driving device 14 to obtain a desired opening region of the collimator 102.

The detector-movement control function 166 accepts information relating to the opening region of the collimator 102, and acquires a movable range of the X-ray detector 111 on a plane parallel to a detecting surface of the X-ray detector 111. That is, the detector-movement control function 166 reads the X-ray irradiation range and current positional information of the X-ray detector 111, to calculate the movable range of the X-ray detector 111. The movable range of the X-ray detector 111 is, for example, a range that the X-ray irradiation range is included in a detecting region of the X-ray detector 111. More specifically, when information relating to movement of the X-ray detecting device 11 is input through the movement operating device 112, the detector-movement control function 166 accepts the input information. Subsequently, the detect movement control function 166 accepts the information about the opening region of the collimator 102 from the collimator control function 165, and the current positional information of the X-ray detector 111 from a sensor 114. The detector-movement control function 166 calculates a detecting region on the X-ray detector 111 with respect to the size of the opening region. For example, when a range of 20 centimeters (cm) square having the common center with the X-ray detector 111 is a use range of the detecting device with respect to the X-ray detector 111 of 40 cm square, the X-ray detector 111 can move 10 cm toward each direction in the parallel direction. Moreover, the detector-movement control function 166 causes, by the X-ray-detector moving device 113, the X-ray detector 111 to make translational movement relative to the X-ray tube 101 within the acquired movable range. The detector-movement control function 166 causes the X-ray detector 111 to make translational movement, for example, in the opening and closing direction of the blades in the collimator 102. That is, the detector-movement control function 166 drives the X-ray-detector moving device 113 so as to move the X-ray detector 111 according to the movable range, by using the information about the calculated movable range of the X-ray detector 111. As one example, the detector-movement control function 16 causes the X-ray detector 111 to make translational movement to an end of the movable range.

For example, the detector-movement control function 166 causes the X-ray detector 111 to make translational movement in a direction toward which a distance from an operator increases within the movable range. Moreover, for example, the detector-movement control function 166 causes the X-ray detector 111 to make translational movement in a direction toward which a distance to the C-ram 12 decreases within the movable range. Specifically, the detector-movement control function 166 moves the X-ray detector 111 based on the distance between the X-ray detector 111 and an operator, or the distance between the X-ray detector 111 and the C arm 12 detected by the sensor 114. The sensor 114 is configured with an optical sensor such as an optical camera, and detects a distance between the X-ray detector 111 and an operator, or a distance between the X-ray detector 111 and the C arm 12 based on an image including the X-ray detector 111, an operator, the C arm 12, or the like. Moreover, the sensor 114 is arranged at four corners of the X-ray detectors 111, configured with a distance sensor (distance image sensor of time of flight (TOF) type, infrared ray sensor, or the like) that measures a distance to a subject, and detects a distance to an operator, or a distance to the C arm 12. In such a case, the sensor 114 can identify a subject being an operator or the C arm 12, based on a direction in which the subject is positioned.

Moreover, for example, the detector-movement control function 166 sets a moving direction and a moving distance of the X-ray detector 111 based on the information about the opening region of the collimator 102 and on input information accepted by the input circuitry 16, and causes the X-ray detector 111 to make translational movement based on the set moving direction and moving distance. Furthermore, the detector-movement control function 166 can display/output information about each moving direction corresponding to the calculated movable range of the X-ray detector 111 on the display 17 and the movement operating device 112. At this time, when the movement operating device 112 is configured with the switches arranged on a side surface of the X-ray detector 111 as shown in FIG. 3, it can be informed by lighting or flashing light only at a switch of a direction for which the detector-movement control function 166 has determined movable, out of the respective switches.

Furthermore, the detector-movement control function 166 can store positional information before movement of the X-ray detector 111 in the storage circuitry 19, and control to return the X-ray detector 111 back to a position before the movement. In such a case, the X-ray diagnostic apparatus 100 includes the storage circuitry 19 that stores a position of the X-ray detector 111. Moreover, in such a case, the detector-movement control function 166 causes the X-ray detector 111 to make translational movement from a state after the movement back to a state before the movement. At this time, for example, by operating the "home" button of the movement operating device 112 by an operator, the X-ray detector 111 can be moved back to the position before the movement. The positional information before movement of the X-ray detector 111 stored in the storage circuitry 19 can be information that indicates a position right before the movement, or any position during the procedure. The positional information of the X-ray detector 111 is calculated from an amount of movement in each direction from a position at which the amount of movement in each parallel direction is 0. When an arbitrary position during the procedure is stored in the storage circuitry 19, it can be configured such that the detector-movement control function 166 receives input information from an operator through the input circuitry 18 or the movement operating device 112, and a positional information of the X-ray detector 111 at that point is stored in the storage circuitry 19. Moreover, it can be configured such that when the X-ray detector 111 and the C arm 12 have not moved for a predetermined time period, positional information of the X-ray detector 111 at that point is stored in the storage circuitry 19.

Furthermore, the detector-movement control function 166 can be configured to set the moving direction of the X-ray detector 111 to a direction in which the moving distance from a current position of the X-ray detector 111 is maximized. For example, the X-ray detector 111 is moved not in one direction relative to an operator, but in a combined direction of a forward direction and left and right directions.

The respective processing functions performed by the system control function 161, the drive control function 162, the X-ray control function 163, the image processing function 164, the collimator control function 165, and the detector-movement control function 166, which are the components of the processing circuitry 16 are stored in the storage circuitry 19 in a form of a computer-executable program. The processing circuit 16 is a processor that reads the program from the storage circuitry 19, and that executes the program thereby implementing the corresponding function. In other words, the processing circuitry 16 that has read the programs is to have the respective function shown in the processing circuitry 16 in FIG. 1. Although the processing functions performed by the system control function 161, the drive control function 162, the X-ray control function 163, the image processing function 164, the collimator control function 165, and the detector-movement control function 166 have been explained to be implemented by a single unit of the processing circuitry 16 in FIG. 1, it can also be configured such that the functions are implemented by respective processors executing the respective programs.

FIG. 7 is a flowchart according to the first embodiment. First, a use mode of the X-ray diagnostic apparatus 100 is determined by an operator. In the first embodiment, a posterior-anterior mode (PA mode) in which the X-ray detecting device 11 is arranged on an upper side relative to the subject P is explained as an example. In the PA mode, as the X-ray detector 111 is arranged right above a subject, the X-ray detector 111 interrupts the sight of an operator. First, the PA mode in which the X-ray detecting device 11 is arranged right above the subject P is selected by an operator (step S101).

Subsequently, the X-ray irradiation range is determined by an operator. An operator refers to an X-ray image that is displayed on the display 17, sets the X-ray irradiation range through the input circuitry 18, and performs X-ray radioscopy for the set X-ray irradiation range (step S102). At this time, in a region outside of the set X-ray irradiation range, an X-ray image in a region outside of the X-ray irradiation range right before the X-ray irradiation range is set can be displayed, by displaying a last image hold (LIH) image.

Subsequently, the detector-movement control function 166 reads the X-ray irradiation range set at step S102 from the collimator control function 165, and reads the positional information of the X-ray detector 111 from the sensor 114, thereby calculating a movable range of the X-ray detector 111 (step S103).

When an operator wishes to check a portion at hand, an operation to move the X-ray detector 111 is performed. At this time, an operator operates the movement operating device 112, and performs an input operation to move the X-ray detector 111 in a desired direction (step S104).

When the movable range of the X-ray detector 111 is calculated at step S103, it is determined whether the X-ray detector 111 is positioned at the moving limit in the moving direction specified by an operator at step S104 (step S105). When the X-ray detector 111 is in such a state that the X-ray detector 111 is to be out of the X-ray irradiation range if the X-ray detector 111 moves in the direction specified by an operator, it is determined that the X-ray detector 111 positioned at the moving limit by the detector-movement control function 166. When the X-ray detector 111 is positioned at the moving limit, the processing is ended (step S105: YES).

When the X-ray detector 111 is not positioned at the moving limit, it proceeds to step S106, and the processing is continued (step S105: NO).

Subsequently, the X-ray detector 111 is moved by the X-ray-detector moving device 113 in the direction specified by an operator at step S104 (step S106).

When the movement of the X-ray detector 111 is performed at step S106, the detector-movement control function 166 determines whether to continue the moving operation of the X-ray detector 111 (step S107). When the moving operation is continued, it returns to step S104, and information about the moving direction of the X-ray detector 111 is accepted again from an operator (step S107: YES). When the moving operation of the X-ray detector 111 is not continued (step S107: NO), the movement of the X-ray detector 111 is ended (step S108).

By performing the series of processing described above, the X-ray diagnostic apparatus 100 in the present embodiment accepts input information from an operator, moves the X-ray detector 111 in a desired direction within the X-ray irradiation range, thereby enabling to insure the sight at hand of an operator, and enabling to support the procedure by an operator.

In the first embodiment, a case in which the moving direction of the X-ray detector 111 by providing the movement operating device 112 and accepting an input operation from an operator has been explained. In a present modification, a case in which input information about the moving direction of the X-ray detector 111 from an operator is accepted from the sensor 114, instead of the movement operating device 112 is explained.

The sensor 114 in the present modification detects, when a force is applied to the X-ray detector 111 by pressing or the like in a desired direction by an operator, a direction to which the force is applied. In other words, the input circuitry 18 in the present modification is provided in the X-ray detector 111, and is constituted of the sensor 114 that detects a moving direction corresponding to the direction toward which a force is applied by an operator. Therefore, the sensor 114 of the present modification is configured with a touch sensor or an acceleration sensor. Detecting the direction toward which the force is applied to the X-ray detecting device 11 by an operator, the sensor 114 outputs the information to the detector-movement control function 166. The detector-movement control function 166 calculates a movable range of the X-ray detector 111, and drives the X-ray-detector moving device 113 according to the movable range. Thus, an operator can move the X-ray detector 111 in a direction wished to move the X-ray detector 111 by applying a force to the X-ray detecting device 11.

Moreover, although the sensor 114 has been explained as one that detects a force applied to the X-ray detector 111 by an operator in the present modification, it can detect just a contact by an operator. In that case, at least one unit of the sensor 114 is arranged on each side surface of the X-ray detector 111, and it can be configured to determine a moving direction of the X-ray detector 111 according to a side surface on which an operator has touched. For example, the X-ray detector 111 moves in a leftward direction when an operator touches a right-side surface of the X-ray detector 111 viewed from an operator, and moves in a forward direction relative to an operator when an operator touches a side surface of the X-ray detector 111 opposing to an operator.

The X-ray diagnostic apparatus 100 according to the modification explained above can move the X-ray detector 111 within the X-ray irradiation range by applying a predetermined force to a direction toward which an operator wishes to move the X-ray detector 111.

In the first embodiment and the first modification of the first embodiment, a case in which an input operation from an operator is accepted to read a moving direction of the X-ray detector 111, and the X-ray detector 111 is moved in the direction has been explained. In a present modification, a case in which the X-ray detector 11 is moved according to a position of an operator and arrangement of the display 17 is explained, referring to FIG. 8A and FIG. 8B.

Figure 8A:
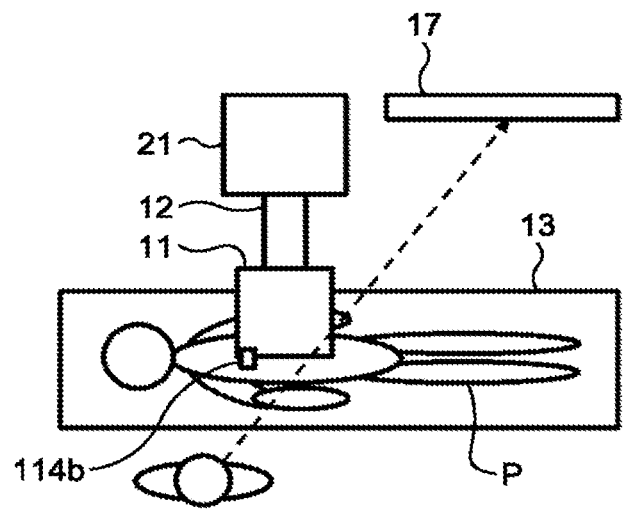
FIG. 8A is a diagram for explaining a structure to move the X-ray detector based on a positional relationship of an operator and a display according to the first embodiment.
Figure 8B:
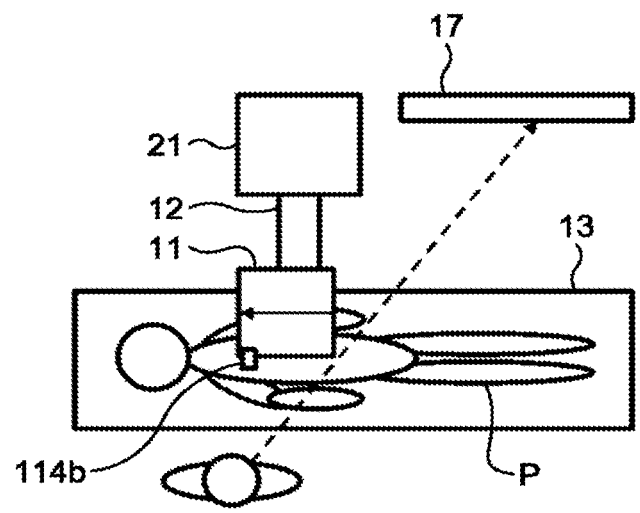
FIG. 8B is a diagram for explaining a structure to move the X-ray detector based on a positional relationship of an operator and the display according to the first embodiment.

FIG. 8A and FIG. 8B are diagrams for explaining the first modification in which the X-ray detector 111 is moved according to a position of an operator, and an arrangement position of the display 17.

In the present modification, a sensor 114b is configured with, for example, an optical sensor such as an optical camera. Moreover, it is preferable that the sensor 114b be configured with a stereo camera constituted of multiple optical cameras to calculate a position of an operator. The sensor 114b is arranged on a side surface of the X-ray detector 111 as shown in FIG. 8A and FIG. 8B. The positional information of an operator acquired by the sensor 114b is transmitted to the detector-movement control function 166. The detector-movement control function 166 moves the X-ray detector 111 according to the positional information of an operator acquired by the sensor 114b. For example, as shown in FIG. 8A, when the X-ray detecting device 11 is positioned on a straight line connecting an operator and the display 17, and the sight of an operator is interrupted by the X-ray detector 111, the detector-movement control function 166 moves the X-ray detector 111 in a leftward direction, a forward direction, and a left-forward direction relative to an operator as shown in FIG. 8B. At this time, the moving distance is within a range not exceeding the X-ray irradiation range similarly to the first embodiment.

The X-ray diagnostic apparatus 100 according to the modification explained above includes a sensor that acquires positional information of an operator and the display 17. Moreover, the detector-movement control function 166 according to the modification explained above calculates a moving direction and a distance of the X-ray detector 111 based on the positional information of the display 17 and an operator acquired by the sensor. That is, the X-ray diagnostic apparatus 100 according to the modification explained above can move the X-ray detector 111 automatically based on the positional information of an operator accepted from the sensor 114. Thus, it becomes possible to insure the sight for an operator to refer to the display 17 during the procedure for the subject P.

In the first embodiment, the case in which the processing circuitry 16 accepts input information from an operator to move the X-ray detector 111, and the case in which the sensor 114 outputs a positional relationship between an operator and the display 17 to the processing circuitry 16 to move the X-ray detector 111 have been explained. In a second embodiment, a case in which the X-ray detector 111 is moved when there is a possibility that the X-ray detector 111 interferes with an operator or the tabletop 13 is explained. First, execution of the PA mode in which the X-ray detector 111 is arranged above the subject P is explained.

Figure 9:
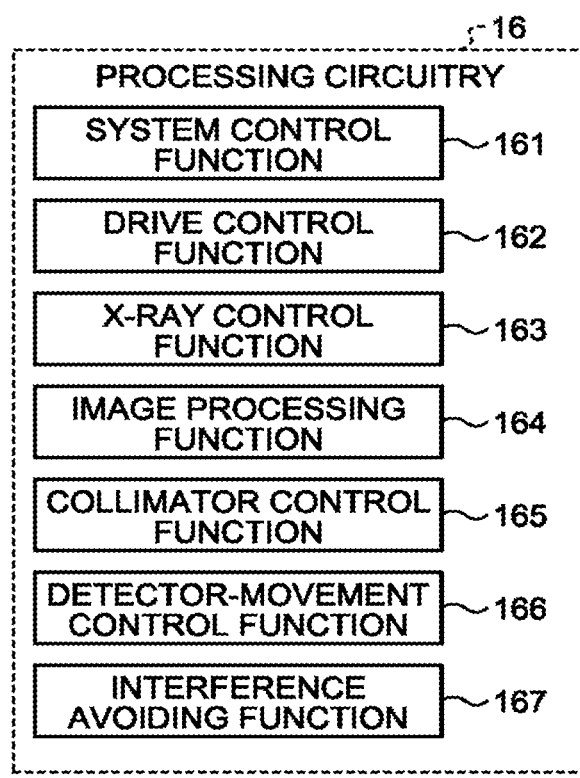
FIG. 9 is a block diagram showing a configuration of processing circuitry according to a second embodiment.

FIG. 9 is a block diagram showing processing circuitry 16b of the X-ray diagnostic apparatus 100 according to the second embodiment. The processing circuitry 16b in the second embodiment has a configuration in which an interference avoiding function 167 is added to the processing circuitry 16 of the first embodiment.

The interference avoiding function 167 has a function of automatically moving the X-ray detector 111 to avoid interference with the tabletop 13 when the X-ray detector 111 comes into contact with an operator or the tabletop 13 by rotational movement of the C arm 12, or when the X-ray detector 111 and an operator or the tabletop 13 come close to each other with a predetermined distance or less. At this time, an input signal from an operator or the like to move the X-ray detector 111 is not necessary. For example, a case in which the X-ray detector 111 comes into contact with an operator as a result of operating the C arm 12 by an operator is explained, using FIG. 10A and FIG. 10B.

Figure 10A:
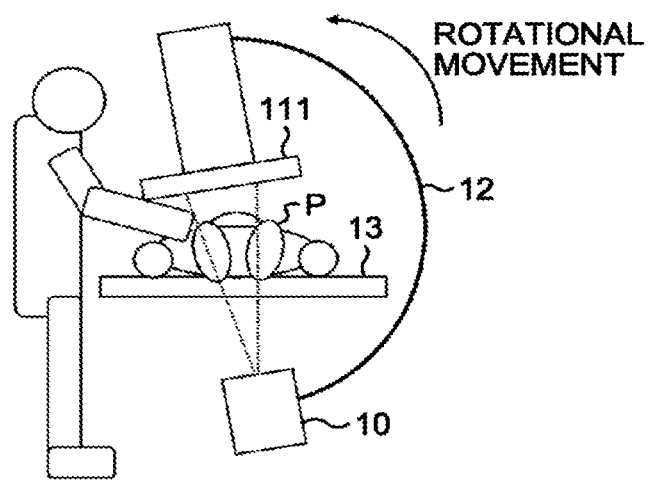
FIG. 10A shows one example of a moving method of the X-ray detector when a C arm according to a second embodiment makes rotational movement.
Figure 10B:
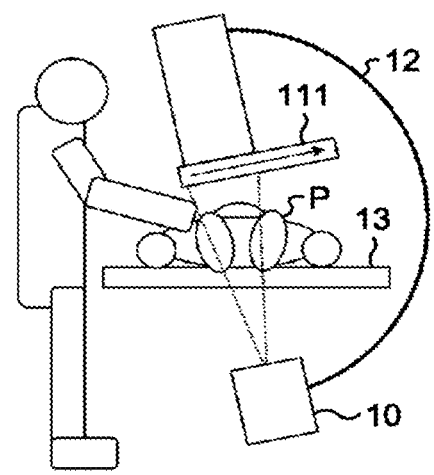
FIG. 10B shows one example of the moving method of the X-ray detector when the C arm according to the second embodiment makes rotational movement.

FIG. 10A shows a case in which the C arm 12 has rotated and is inclined relative to the tabletop 13 by predetermined angle from the horizontal direction and the X-ray detector 111 is in contact with an operator. The interference avoiding function 167 detects that the X-ray detector 111 interferes therewith, through the sensor 114, when the C arm 12 in a rotated state comes into contact with an operator, or comes close thereto with a predetermined distance or less. For example, the sensor 114 is configured with a touch sensor, an acceleration sensor, or the like, and the sensor 114 detects that an operator and the X-ray detector 111 come into contact with each other. The interference avoiding function 167 thereby detects that the X-ray detector 111 interferes therewith. Moreover, for example, the sensor 114 is configured with an optical sensor such as an optical camera, and the sensor 114 detects that the distance between an operator and the X-ray detector 111 becomes a predetermined distance or less. The interference avoiding function 167 thereby detects that the X-ray detector 111 interferes therewith. The sensor 114 outputs information indicating interference to the interference avoiding function 167. The interference avoiding function 167 reads the input information from the sensor 114, and receives information about a direction and a range in which the X-ray detector 111 can move, and moves the X-ray detector 111 in a direction not interfering with an operator, that is, in a direction toward which the direction to the tabletop increases, as shown in FIG. 10B.

The X-ray diagnostic apparatus 100 according to the second embodiment explained above includes the sensor 114 that acquires positional information of the X-ray detector 111. Moreover, the interference avoiding function 167 according to the second embodiment explained above reads the positional information of the X-ray detector 111 from the sensor 114, and causes the X-ray detector 111 to make translational movement with rotational movement of the C arm 12. That is, in the second embodiment explained above, the X-ray diagnostic apparatus 100 that is capable of moving the X-ray detector 111 automatically with movement of the C arm 12 so as not to be in contact with an operator can be provided.

In a modification of the second embodiment, execution in the AP mode in which the X-ray detector 111 is arranged below the subject P is explained. In the AP mode, a subject of interference by the X-ray detector 111 is mainly the tabletop 13.

Figure 11A:
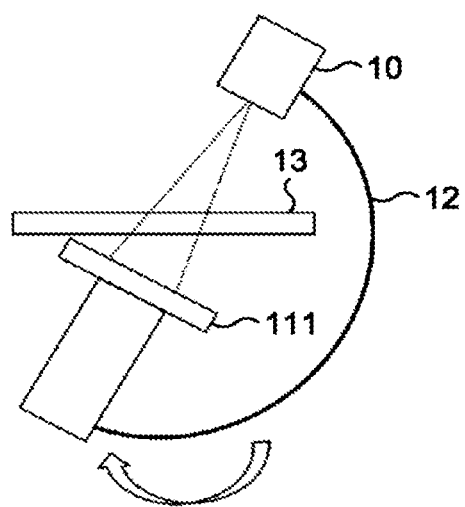
FIG. 11A is a schematic diagram showing one example of movement of an X-ray detector according to the second embodiment.
Figure 11B:
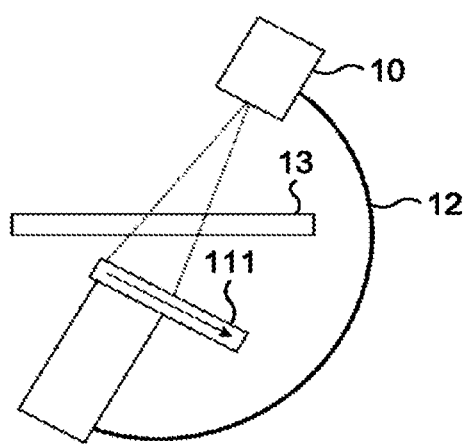
FIG. 11B is a schematic diagram showing one example of movement of the X-ray detector according to the second embodiment.

FIG. 11A and FIG. 11B are diagrams for explaining a configuration of the modification of the second embodiment. FIG. 11A shows a case in which the C arm 12 rotates as a result of operation by an operator, and the X-ray detector 111 that is arranged below the tabletop 13 comes close to the tabletop 13. In the present modification, similarly to the second embodiment, when the sensor 114 detects that the X-ray detector 111 and the tabletop 13 interfere with each other or come close to each other with a predetermined distance or less, the interference avoiding function 167 moves the X-ray detector 111 to avoid interference of the X-ray detector 111 with the tabletop 13 as shown in FIG. 11B. That is, the interference avoiding function 167 according to the present modification causes the X-ray detector 111 to make translational movement in a direction toward which a distance between the X-ray detector 111 and the tabletop 13 increases, with rotational movement of the C arm 12.

FIG. 12 is a flowchart showing a series of processing in the AP mode, which is the modification of the second embodiment. First, a use mode of the X-ray diagnostic apparatus 100 is determined by an operator. First, the AP mode in which the X-ray detecting device 11 is arranged below the subject P is selected by an operator (step S201).

Subsequently, the X-ray irradiation range is determined by an operator. An operator refers to an X-ray image displayed on the display 17, and sets the X-ray irradiation range through the input circuitry 18, to perform X-ray radioscopy (step S202).

When the X-ray radioscopy is performed in the X-ray irradiation range set at step S202, if it is desired to observe a region of interest of the subject P from a different angle, an operator operates to rotate the C arm 12 to change an X-ray irradiation angle (step S203).

When the X-ray detector 111 interferes with the Tabletop 13 as a result of rotation operation of the C arm 12 at step S203, or when the interference avoiding function 167 detects that they come close to each other with a predetermined distance or less (step S204), the detector-movement control function 166 accepts the information, and a movable range of the X-ray detector 111 is calculated (step S205).

When the movable range of the X-ray detector 111 is calculated at step S205, it is determined, by the interference avoiding function 167, whether the X-ray detector 111 can be moved in a direction opposite to the rotation direction of the C arm 12 operated by an operator at step S203 (step S206). At this time, when the X-ray detector 111 cannot be moved, it proceeds to step S208, and an operator determines whether it is necessary to stop the rotation of the C arm 12. When the X-ray detector 111 can be moved, it proceeds to step S207, and the processing is continued.

When it is determined that the X-ray detector 111 can be moved by the interference avoiding function 167 at step S206, the X-ray detector 111 is moved in a direction not interfering with the tabletop 13 (step S207).

When the X-ray detector 111 is moved at step S207, an operator determines whether it is necessary to stop the rotation of the C arm 12. If the rotation of the C arm 12 is stopped, a series of processing is ended. If the rotation of the C arm 12 is not stopped, and the C arm 12 is, for example, rotated in another angle, or the like, it returns to step S203, and the processing at step S203 and later is continued (step S208).

As described, by performing a series of processing, the X-ray detector 111 can be moved automatically to a direction not interfering with the tabletop 13 when the X-ray detector 111 interferes with the tabletop 13 comes close to each other with a predetermined distance or less as a result of performing imaging by changing the angle of the C arm 12 at the time of performing X-ray imaging of the subject P in the AP mode.

Furthermore, although in the second embodiment explained above, it has been explained such that the sensor 111 is used and the X-ray detector 111 is moved when the X-ray detector 111 interferes with an operator or the tabletop 13, or when the X-ray detector 111 comes close to an operator or the tabletop 13 with a predetermined distance or less, the present embodiment is not limited to the above configuration. For example, it can be configured such that when the C-arm state detector that is provided in the C-arm driving device 121 detects that an angle between a straight line connecting the X-ray detecting device 11 and the X-ray generating device 10 of the C arm 12 and a plane perpendicular to a floor surface changes by a predetermined angle or more, the detector-movement control function 166 moves the X-ray detector 111. At this time, the detector-movement control function 166 accepts angle information of the C arm 12 from the C-arm state detector, and calculates an amount of movement of the X-ray detector 111 according the angle of the C arm 12.

Although the amount of movement of the X-ray detector 111 is explained to be calculated from the X-ray irradiation range on the X-ray detector 111 in the embodiment explained above, the amount of movement of the X-ray detector 111 can be calculated using a region of interest or an opening region of the collimator 102. In this case, the amount of movement of the X-ray detector 111 cannot be calculated directly from the size of the region of interest or the opening region of the collimator 102. Therefore, it is required to calculate the amount of movement based on the size of the region of interest or the opening region of the collimator 102, and on the SID value.

In the embodiment explained above, when the X-ray detector 111 moves, a position at which an X-ray radioscopic image is displayed on the display 17 is to be off the center of the display 17 with movement of the X-ray detector 111. Therefore, when the X-ray detector 111 is moved, it is preferable that the position of the X-ray radioscopic image on the display 17 be shifted to the center according to the amount of movement of the X-ray detector 111. For example, when the X-ray detector 111 is moved toward a right forward direction relative to an operator, the X-ray radioscopic image on the display 17 is displayed such that the center thereof is positioned at an upper right part of a screen of the display 17. Therefore, it is preferable that the central position of the X-ray radioscopic image to be displayed be shifted to the center of a display screen of the display 17. Therefore, the display 17 shifts a display position of an X-ray image to be displayed when the X-ray detector 111 is moved, to a central position according to the amount of movement of the X-ray detector 111. Thus, it becomes possible to provide a screen display easy for an operator to visually recognize even when the X-ray detector 111 is moved.

According to the embodiment explained above, it becomes possible to move the X-ray detector 111 toward a desirable direction by using input information from an operator, or positional information of the X-ray detector 111, an operator, the display 17, and the like acquired by the sensor 114, and the like. Thus, it becomes possible for an operator to check a state at hand without changing an X-ray radioscopic image that is currently being observed during treatment of the subject P, and to provide the X-ray diagnostic apparatus 100 that can support procedure of an operator.

Note that as for a component expressed as "unit" in the present embodiment, an operation thereof can be implemented by hardware, or by software, or by combination of hardware and software.

According to the X-ray diagnostic apparatus of the embodiments, a procedure performed by an operator can be proceeded smoothly.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
a tabletop on which a subject is placed;
an arm configured to support an X-ray tube irradiating an X-ray and a detector that detects the X-ray such that the X-ray tube and the detector oppose to each other sandwiching the subject;
a collimator configured to narrow an irradiation range of the X-ray;
a detector moving equipment configured to cause the detector to make translational movement; and
processing circuitry configured
to control the collimator,
to accept information about an opening region of the collimator to acquire a movable range of the detector on a plane parallel to a detecting surface of the detector, wherein the movable range is a range that enables an irradiation region of the X-ray to be included in a detecting region of the detector without change of the irradiation range, and
to cause, by the detector moving equipment, the detector to make translational movement relative to the X-ray tube within the acquired movable range.

2. The X-ray diagnostic apparatus according to claim 1, wherein
the processing circuitry is configured to cause the detector to make translational movement up to an end of the movable range.

3. The X-ray diagnostic apparatus according to claim 1, wherein
the collimator is configured to include at least one pair of blades, and
the processing circuitry is further configured
to control the collimator by controlling opening and closing of the blades, and
to cause the detector to make translational movement in a direction of opening and closing of the blades.

4. The X-ray diagnostic apparatus according to claim 1, wherein
the processing circuitry is configured to cause the detector to make translational movement toward a direction in which a distance to an operator increases, within the movable range.

5. The X-ray diagnostic apparatus according to claim 1, wherein
the processing circuitry is configured to cause the detector to make translational movement toward a direction in which a distance to the arm decreases, within the movable range.

6. The X-ray diagnostic apparatus according to claim 1, further comprising:
input circuitry configured to accept input information from an operator, wherein
the processing circuitry is configured to set a moving direction and a moving distance of the detector based on information about the opening region of the collimator, and the input information accepted by the input circuitry.

7. The X-ray diagnostic apparatus according to claim 6, wherein
the input circuitry is configured to be provided in the detector, and is configured with a switch that accepts a moving direction of the detector from an operator.

8. The X-ray diagnostic apparatus according to claim 6, wherein
the input circuitry is configured to be provided in the detector, and is configured with a sensor that detects a moving direction corresponding to a direction in which a force is applied by an operator.

9. The X-ray diagnostic apparatus according to claim 1, further comprising:
a display configured to display an X-ray image that is generated based on an X-ray detected by the detector; and
a sensor configured to acquire positional information of an operator and the display, wherein
the processing circuitry is further configured to calculate a moving direction and a distance of the detector based on the positional information of the display and an operator acquired by the sensor.

10. The X-ray diagnostic apparatus according to claim 1, further comprising
a sensor configured to acquire positional information of the detector, wherein
the processing circuitry is further configured to read positional information of the detector, and cause the detector to make translational movement with rotational movement of the arm.

11. The X-ray diagnostic apparatus according to claim 10, wherein
the processing circuitry is further configured to cause the detector to make translational movement in a direction toward which a distance to the tabletop increases, with the rotational movement of the arm.

12. The X-ray diagnostic apparatus according to claim 1, further comprising:
storage circuitry configured to store a position of the detector, wherein
the processing circuitry is further configured to cause the detector to make translational movement to be in a state before movement from a state after movement of the detector.

13. The X-ray diagnostic apparatus according to claim 1, further comprising:
a display configured to display an X-ray image that is generated based on the X-ray detected by the detector, wherein
the display is configured to shift a display position of an X-ray image to be displayed when the detector is moved, to a central position according to an amount of movement of the detector.

14. The X-ray diagnostic apparatus according to claim 1, wherein
the arm is a C arm configured to support the X-ray tube and the detector so as to oppose each other.

15. The X-ray diagnostic apparatus according to claim 14, wherein
the C arm is configured to be arranged so as to sandwich the tabletop along a short side direction of the tabletop.

\* \* \* \* \*